(12) United States Patent
Shin

(10) Patent No.: US 9,506,809 B2
(45) Date of Patent: Nov. 29, 2016

(54) PORTABLE DEVICE FOR MEASURING TEMPERATURE USING INFRARED ARRAY SENSOR

(75) Inventor: Jae-Woo Shin, Seoul (KR)

(73) Assignee: EASYTEM CO., LTD. (KR)

( * ) Notice: Subject to any disclaimer, the term of this patent is extended or adjusted under 35 U.S.C. 154(b) by 608 days.

(21) Appl. No.: 13/885,161

(22) PCT Filed: Nov. 16, 2011

(86) PCT No.: PCT/KR2011/008753
§ 371 (c)(1),
(2), (4) Date: May 13, 2013

(87) PCT Pub. No.: WO2012/067423
PCT Pub. Date: May 24, 2012

(65) Prior Publication Data
US 2013/0235901 A1    Sep. 12, 2013

(30) Foreign Application Priority Data
Nov. 17, 2010   (WO) ................ PCT/KR2010/008119

(51) Int. Cl.
*G01J 5/60*    (2006.01)
*G01J 5/00*    (2006.01)
(Continued)

(52) U.S. Cl.
CPC .. *G01J 5/60* (2013.01); *A61B 5/01* (2013.01); *A61B 5/70* (2013.01); *A61B 5/743* (2013.01); *G01J 5/0025* (2013.01); *G01J 5/025* (2013.01); *G01J 5/0265* (2013.01); *G01J 5/089* (2013.01); *G01J 5/0859* (2013.01); *G01K 1/20* (2013.01); *G01J 5/0275* (2013.01);
(Continued)

(58) Field of Classification Search
CPC ...... G01J 5/0025; G01J 5/025; G01J 5/0265; G01J 5/089; G01J 5/0859; G01J 5/60; G01J 2005/0081; G01J 2005/106; G01J 2005/0077; G01J 5/0275; A61B 5/01; A61B 5/70; A61B 5/743; G01K 1/20
USPC .............................................................. 3/121
See application file for complete search history.

(56) References Cited

U.S. PATENT DOCUMENTS

| | | | |
|---|---|---|---|
| 5,012,813 | A | 5/1991 | Pompei et al. |
| 6,056,435 | A | 5/2000 | Pompei |
| 6,299,347 | B1 | 10/2001 | Pompei |
| 6,499,877 | B2 | 12/2002 | Pompei |

(Continued)

FOREIGN PATENT DOCUMENTS

| | | |
|---|---|---|
| CN | 1507742 A | 6/2004 |
| CN | 2669153 | 1/2005 |

(Continued)

*Primary Examiner* — Lisa Caputo
*Assistant Examiner* — Philip Cotey

(57) ABSTRACT

Disclosed is a portable device for measuring temperature with infrared array sensor. This portable device includes: an infrared array sensor module for taking temperature values in a unit of pixel and including a plurality of infrared sensors arranged in an array of pixels; a controller for calculating a resultant temperature value of a subject with reference to the temperature values taken each by the sensors; a display for expressing the resultant temperature value calculated by the controller; and a view finder with an indicator defining a target point to be measured for temperature and having a profile corresponding to the whole or a local shape of the subject. The view finder is formed of a transparent plate on which the subject's shape is reflected. The transparent plate is formed of: a notch representing the indicator; and a lens at least provided in the indicator.

13 Claims, 19 Drawing Sheets

(51) Int. Cl.
*G01J 5/02* (2006.01)
*G01J 5/08* (2006.01)
*G01K 1/20* (2006.01)
*A61B 5/00* (2006.01)
*A61B 5/01* (2006.01)
*G01J 5/10* (2006.01)

(52) U.S. Cl.
CPC ............. *G01J 2005/0077* (2013.01); *G01J 2005/0081* (2013.01); *G01J 2005/106* (2013.01)

(56) References Cited

U.S. PATENT DOCUMENTS

| | | | |
|---|---|---|---|
| 6,669,362 | B1 | 12/2003 | Lin et al. |
| 7,314,309 | B2 | 1/2008 | Pompei |
| 7,787,938 | B2 | 8/2010 | Pompei |
| 8,971,997 | B2 | 3/2015 | Oral et al. |
| 2001/0045463 | A1 | 11/2001 | Madding et al. |
| 2002/0143257 | A1* | 10/2002 | Newman ............ G01J 5/02 600/474 |
| 2003/0099277 | A1 | 5/2003 | Bellifemine |
| 2004/0013423 | A1* | 1/2004 | Wells ............... G03B 13/08 396/296 |
| 2005/0094705 | A1 | 5/2005 | Chi |
| 2006/0043303 | A1* | 3/2006 | Safai ............... G01N 21/954 250/347 |
| 2007/0153871 | A1 | 7/2007 | Fraden |
| 2008/0099678 | A1 | 5/2008 | Johnson et al. |
| 2010/0292952 | A1* | 11/2010 | Pomper ............ G01J 5/02 702/135 |
| 2011/0175145 | A1* | 7/2011 | Tsuji ............... G01J 5/02 257/252 |
| 2013/0235901 | A1 | 9/2013 | Shin |

FOREIGN PATENT DOCUMENTS

| | | |
|---|---|---|
| CN | 1880950 B | 12/2006 |
| CN | 101067710 B | 11/2007 |
| CN | 101111748 A | 1/2008 |
| CN | 101876569 A | 11/2010 |
| CN | 201622386 U | 11/2010 |
| GB | 2173297 | 10/1986 |
| JP | 5462880 | 5/1979 |
| JP | 1105125 | 4/1989 |
| JP | 337529 | 2/1991 |
| JP | 4152932 A | 5/1992 |
| JP | 9218100 | 8/1997 |
| JP | 11113858 | 4/1999 |
| JP | 200199714 | 4/2001 |
| JP | 2001166369 | 6/2001 |
| JP | 2001281060 A | 10/2001 |
| JP | 2004138439 A | 5/2004 |
| JP | 2004528085 A | 9/2004 |
| JP | 2005249723 | 9/2005 |
| JP | 2006292488 A | 10/2006 |
| JP | 2009162571 | 7/2009 |
| JP | 2010181324 A | 8/2010 |
| JP | 2010194074 | 9/2010 |
| KR | 20050092480 A | 9/2005 |
| KR | 100682457 B1 | 2/2007 |
| WO | 2007054821 A | 5/2007 |
| WO | 2009074783 A1 | 6/2009 |
| WO | 2011102469 A1 | 8/2011 |

* cited by examiner

-- PRIOR ART --

-- PRIOR ART --

-- PRIOR ART --

-- PRIOR ART --

PORTABLE DEVICE FOR MEASURING TEMPERATURE USING INFRARED ARRAY SENSOR

BACKGROUND

1. Technical Field

The present invention relates generally to measurement for thermal pictures corresponding to infrared rays arising from subjects such as material or human bodies. In particular, this invention is concerned with a device for measuring temperature of a subject with an infrared array sensor capable of detecting a thermal picture from the subject, and a method for measuring temperature the subject entirely or locally by means of the device.

2. Related Art

Nowadays in various technical fields are widely being used thermal detection devices for sensing temperature from material or human bodies in response to even minute infrared rays.

For instance, a thermal detection device automatically turning on/off a lamp at gloomy spot and others, as shown in FIG. 1, is composed including pyroelectric sensor 10, amplifier (AMP) 11, low pass filter (LPF) 12, comparator 13, timer 14, driver 15, lamp 16 and light sensor 17.

In such a thermal detection device, pyroelectric sensor 10 accepts a minute infrared ray from for example a human body and generates an electric signal of low voltage corresponding to the infrared ray. Then, amplifier 11 operates to amplify the low-voltage electric signal up to an electric signal over a predetermined voltage.

During this, low pass filter 12 remove noises, e.g. high frequency noises, while amplifying the electric signal over the predetermined voltage.

Comparator 13 functions to compare the electric signal, which is higher than the predetermined voltage without high frequency noises, with reference voltage V_ref predetermined at for example 0.7V. If a compared result is higher than the reference voltage, timer 14 begins to operate.

Driver 15 supplies power toward lamp 16 to turn lamp 16 on during a definite time (e.g. 10 seconds) for which timer 14 is operating. Here, light sensor 17 generates an electric signal corresponding to light incident thereon in response to circumferential brightness, enabling or disabling an operation of comparator 13.

Summarily, the conventional thermal detection device shown in FIG. 1 operates with the aforementioned configuration such that pyroelectric sensor 10 enables lamp 16 to be automatically turned on when a person is closing thereto in a gloomy spot. In the thermal detection device shown in FIG. 1, as well known, pyroelectric sensor 10 employs a dielectric effecting having a pyroelectric effect. However, pyroelectric sensor 10 is disadvantageous upon which it is impossible to detect a material or human body standing without movement because it does not further generate any electric signal if infrared rays are continuously incident thereon.

To amend such shortness for thermal detection, there has been proposed another thermal detection device employing thermopile sensor 20, instead of pyroelectric sensor 10 of FIG. 1, as shown FIG. 2. Thermopile sensor 20 is a kind of thermal sensor mostly used for measuring a standing material or human body in a non-contacting mode.

Meanwhile, FIG. 3 shows that in recent years there is developing a thermopile array sensor (TAS) fabricated in a single module in which a plurality of thermopile sensors are arranged in square pixel array (e.g. 32×32).

The thermopile array sensors (TAS) are being adopted in advancing units for measuring thermal pictures of material or human bodies. A typical thermal picture measurement unit is shown in FIG. 4, which is composed including thermopile array sensor 30, amplifier (AMP) 31, low pass filter (LPF) 32, first analogue-digital converter (ADC) 33, second analogue-digital converter 34, digital signal processor 35 and display device 36.

Thermopile array sensor 30, for example, is formed of a module in which a plurality of thermopile sensors are arranged in square pixels to correspondingly detect temperature from respective parts (e.g. 32×32) of an subject. In addition, thermopile array sensor 30 includes temperature sensor TS, such as thermistor, for detecting internal temperature of the module.

Temperature sensor TS outputs an electric signal corresponding to internal temperature of the module. The thermopile sensors of thermopile array sensor 30 accepts infrared rays in the unit of pixel respectively from parts of an subject and then output electric signals corresponding each to the infrared rays.

Amplifier 31 operates to amplify the electric signals output from the thermopile array sensor 30. Low pass filter 32 removes high frequency noises from the electric signals. First analogue-digital converter 33 transforms the noise-removed electric signal from analogue component into digital component.

Second analogue-digital converter 34 transforms the electric signal, which is output from temperature sensor TS, from analogue component into digital component. Digital signal processor 35 outputs a difference from comparison between the digital signals transformed by first and second analogue-digital converter 33 and 34, computing temperature values of respective parts on the subject.

As an example, if internal module temperature detected by temperature sensor TS is 10° C. and temperature of a first part of the subject, which is detected by first pixel $P_{(1,1)}$ of thermopile array sensor 30 is 45° C., a thermal difference between them is calculated to determined the first part's temperature as being 35° C. As also, if temperature of a second part of the subject, which is detected by second pixel $P_{(1,2)}$ of thermopile array sensor 30 is 46° C. when internal module temperature detected by temperature sensor TS is 10° C., a thermal difference between them is calculated to determined the second part's temperature as being 36° C.

After generating a thermal picture corresponding to those thermal difference values respective to the parts of the subject, it is represented on display device 36, such as monitor or others, as exemplified in FIG. 4. Thereby, a user is able to identify a thermal distribution state of the subject or other thermal conditions thereof through the thermal picture represented on a monitor or other display unit.

However, in detecting thermal conditions only from specific parts of human body (e.g. forehead, ear, hand, or another part in human body) by means of the aforementioned thermal picture measurement units, it could be inconvenient on use because it is necessary to carefully adjust a distance and angle between a subject's part and the thermal picture measurement unit. If a distance and angle for measurement is unsuitably adjusted, it will result in a serious error in detecting temperature and/or thermal distribution from a subject.

In order to make a general thermopile sensor have a reasonable temperature value for thermal measurement by infrared rays, it needs to detect temperature from a sensor itself before obtaining a voltage output for temperature from a subject or target. In the conventional art, as it is assumed that a sensor's temperature is equal to its ambient temperature, the ambient temperature is used as the sensor's one. Referring to the arts disclosed in U.S. Pat. Nos. 5,012,813, 6,056,435, 6,299,347, 6,499,877, 7,314,309 and 7,787,938, a temperature sensor detecting its own temperature operates by the thermistor mode characterized in nonlinear log function, so that it could be slower in response rate and lower in accuracy of ambient temperature. Especially, since only one sensor was used for measuring its own temperature, it could be inevitable to result in lower accuracy on thermal detection.

Otherwise, in the former U.S. Pat. Nos. 5,012,813, 6,056,435, 6,299,347, 6,499,877, 7,314,309 and 7,787,938 was considered an ambient temperature value Ta applied to a conversion formula of core temperature Tc as the resultant bodily temperature in order to correct an actual bodily temperature in accordance with thermal variation of the circumference. However, in case ambient temperature goes down to be lower than 18° C., it should be additionally considered and corrected about thermal descent on the skin because an optical part as well as the sensor becomes lower in temperature and an operation amplifier of the system varies in thermal coefficient.

Furthermore, with the former U.S. Pat. Nos. 5,012,813, 6,056,435, 6,299,347, 6,499,877, 7,314,309 and 7,787,938, it was impossible to correct erroneous distance measurement arising from a non-contacting mode because it was just capable to accept one-channel (or one-pixel) information but the forms of array. Such one-pixel information cannot provide any way of finding out an actual distance from a subject to be detected. For instance, as disclosed in PCT/IB2006/003859, it needs an additional subsidiary for concentrating focuses onto a pair of light emission devices (LED). Moreover, the prior non-contacting measurement is incapable of detecting or correcting a shake or movement of a thermometer or subject, the reason of which is caused from that thermal data only by one pixel is insufficient to differentiate a subject's motion from a thermal variation.

In the meantime, the prior arts U.S. Pat. No. 7,787,938 and PCT/IB2006/003859 had to scan temperature by contacting a thermometer to a forehead or by spacing a thermometer out in a distance about 5 cm from a forehead in order to find a peak value of the skin around the forehead. This is because it inevitable to shift the thermometer toward a point of the highest temperature as a sensor has only one pixel. But, there are personal differences in distribution of temporal arteries, as like that the higher temperature point is found around a forehead, around a mouth, or at a temple. Consequently, the former technologies just provide means for scanning a forehead and the around thereof, being insufficient to scan and detect temperature from the whole face, so that it is difficult to exactly detect temperature from a person who has higher temperature at other facial points rather than his forehead.

SUMMARY

Accordingly, the present invention is directed to provide a portable device and method, using an infrared array sensor, capable of measuring thermal pictures and bodily temperature more conveniently and exactly by selecting specific parts of material or human body, e.g. forehead, ear, hand, etc.

In an embodiment, a portable device for measuring temperature may comprise: an infrared array sensor module configured to take temperature values in a unit of pixel, including a plurality of infrared sensors arranged in an array of pixels; a controller configured to calculate a resultant temperature value of a subject with reference to the temperature values taken each by the sensors; a display configured to express the resultant temperature value calculated by the controller; and a view finder configured to have an indicator defining a target point to be measured for temperature and having a profile corresponding to the whole or a local shape of the subject. The view finder may be formed of a transparent plate on which the subject's shape is reflected. The transparent plate may be formed of: a notch representing the indicator; and a lens at least provided in the indicator.

The display may be a transparent LCD panel and the view finder may be configured to overlap with the LCD panel in a predetermined interval. The LCD panel may be configured to include a marker that is same with the indicator of the view finder in shape.

The portable device may be further comprised of an LED under the view finder, wherein the notch is configured to make light reflected vertically on the plate from the LED.

The controller may be configured to, if temperature values measured each by the infrared sensors are within a predetermined range, determine that pixels corresponding to the infrared sensors are valid pixels, and calculate a resultant temperature value of the subject with reference to the temperature values measured by the infrared sensors corresponding to the valid pixels. The controller may be also configured to calculate an ambient temperature value from the temperature values measured by infrared sensors corresponding to other pixels except the valid pixels, and correct the resultant temperature value of the subject with reference to the ambient temperature value.

Moreover, according to the present invention, a device for measuring temperature may comprise: an infrared array sensor module configured to take thermal picture information of a subject, including a plurality of infrared sensors arranged in an array of pixels; an on-screen display module configured to generate an indicator having a profile corresponding to an entire or local shape of the subject and defining a target point to be measured for temperature; a display module configured to express the indicator and the thermal picture information; and a controller configured to enable the infrared array sensor module to measure the subject's temperature if the target point displayed by the thermal picture information overlaps with the indicator while the thermal picture information is expressed on the display module along with the indicator.

This device may further comprise a camera module configured to take image information. In this case, the display module may overlap the image information with the indicator. The controller may enable the infrared array sensor module to measure the subject's temperature if the target point displayed by the thermal picture information overlaps with the indicator while the image information is expressed on the display module along with the indicator.

In addition, the controller may determine that pixels included in the indicator are valid pixels if the target point overlaps with the indicator, and then calculate a resultant temperature value of the subject with reference to temperature values measured by infrared sensors respective to the valid pixels. The controller may also calculate an ambient temperature value with reference to temperature values measured by the infrared sensors respective to other pixels except the valid pixels, and then correct the resultant temperature value with reference to the ambient temperature value.

In the meantime, the controller may, if temperature values measured each by the infrared sensors are within a predetermined temperature range, determine that pixels corresponding to the infrared sensors are valid pixels, and calculate a resultant temperature value of the subject with reference to temperature values measured by the infrared sensors corresponding to the valid pixels. And, the controller may calculate an ambient temperature value from temperature values measured by infrared sensors corresponding to other pixels except the valid pixels, and correct the resultant temperature value of the subject with reference to the ambient temperature value.

As another aspect of the present invention, a method for measuring temperature may comprise the steps of: taking thermal picture information of a subject by an infrared array sensor; generating an indicator that has a profile to a target point of the subject and displaying the indicator along with the thermal picture information; measuring temperature from the subject by the infrared array sensor if the target point displayed by the thermal picture information overlaps with the indicator; and calculating and displaying a resultant temperature value of the subject with reference to temperature values measured by a plurality of infrared sensors included in the infrared array sensor.

In an embodiment, a method for measuring temperature may comprise the steps of: taking image information of a subject by a camera module; generating an indicator that has a profile to a target point of a subject and displaying the indicator along with the image information; measuring temperature from the subject by the infrared array sensor if the target point displayed by the thermal picture information overlaps with the indicator; and calculating and displaying a resultant temperature value of the subject with reference to temperature values measured by a plurality of infrared sensors included in the infrared array sensor.

Especially, the step of calculating and displaying the resultant temperature value may be comprised of: determining pixels, which are included in the indicator, as valid pixels; and calculating the resultant temperature value of the subject with reference to temperature values measured by the infrared sensors corresponding to the valid pixels. In this case, the step of calculating and displaying the resultant temperature value is may be comprised of: calculating an ambient temperature value from temperature values measured by the infrared sensors corresponding to other pixels except the valid pixels; and correcting the resultant temperature value with reference to the ambient temperature value.

In another embodiment, the step of calculating and displaying the resultant temperature value may be comprised of: determining that, if temperature values measured each by the infrared sensors are within a predetermined temperature range, pixels corresponding to the infrared sensors are valid pixels; and calculating the resultant temperature value from temperature values measured by the infrared sensors corresponding to the valid pixels. In this case, the step of calculating and displaying the resultant temperature value may be comprised of: calculating an ambient temperature value from temperature values measured by the infrared sensors corresponding to other pixels except the valid pixels; and correcting the resultant temperature value with reference to the ambient temperature value.

According to the device and method of the present invention, for example, temperature at a specific part on an subject is measured through an infrared sensor module, after displaying an indicator corresponding to the specific part of the subject to be detected in temperature, when a picture of the specific part on the subject overlaps with an indicator. Therefore, temperature can be detected at the optimum condition of distance and angle to the subject, achieving more accurate measurement.

In addition, it is permissible to sort valid pixels to a target point of a subject to be detected and measure accurate temperature from the target point on basis of the valid pixel selection. For instance, a user is able to select a specific part of a person, e.g. forehead, ear, hand, etc., and measures temperature from the specific part more conveniently and exactly, enhancing reliability of measuring temperature and thermal distribution as well as easiness on use.

Furthermore, it is possible to calculate the ambient temperature value from invalid pixels around valid pixels and then correct an infrared sensor's own value with reference to the ambient temperature value. This enables more accurate correction than the conventional that just calculate an ambient temperature value by an internal temperature sensor, hence further raising reliability for a result of thermal detection.

Particularly, in case of using a view finder as the indicator, it is more finable to adjust a distance and angle to a subject, hence improving accuracy for temperature measurement and reliability of measured results.

A further understanding of the nature and advantages of the present invention herein may be realized by reference to the remaining portions of the specification and the attached drawings.

BRIEF DESCRIPTION OF THE DRAWINGS

The present invention is illustrated by way of example, and not by way of limitation, in the figures of the accompanying drawings and in which like reference numbers refer to similar elements and in which.

DESCRIPTION OF EMBODIMENTS

Hereinafter, various exemplary embodiments about a device and method for measuring temperature with infrared array sensor will now be described more fully with reference to the accompanying drawings.

Figure 1:
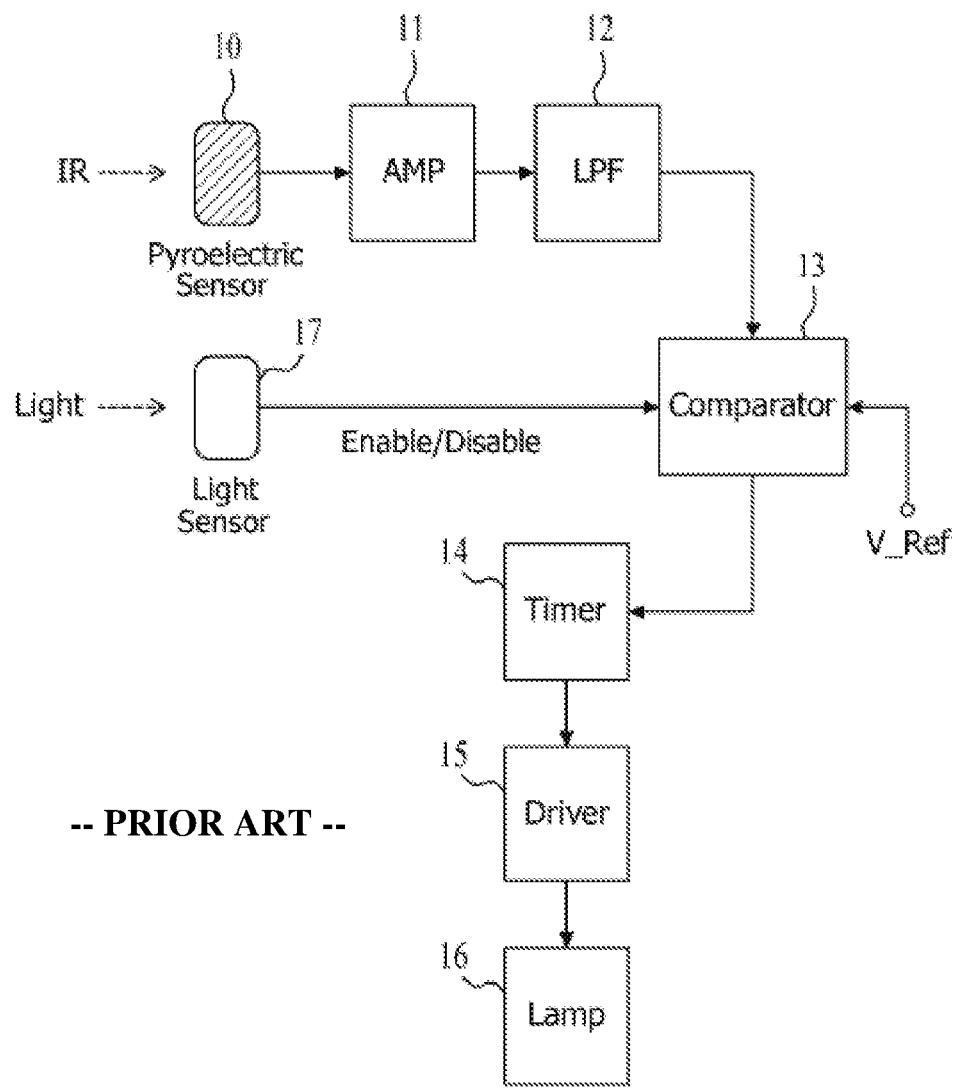
FIG. 1 illustrates a thermal detection device employing a pyroelectric sensor.
Figure 2:
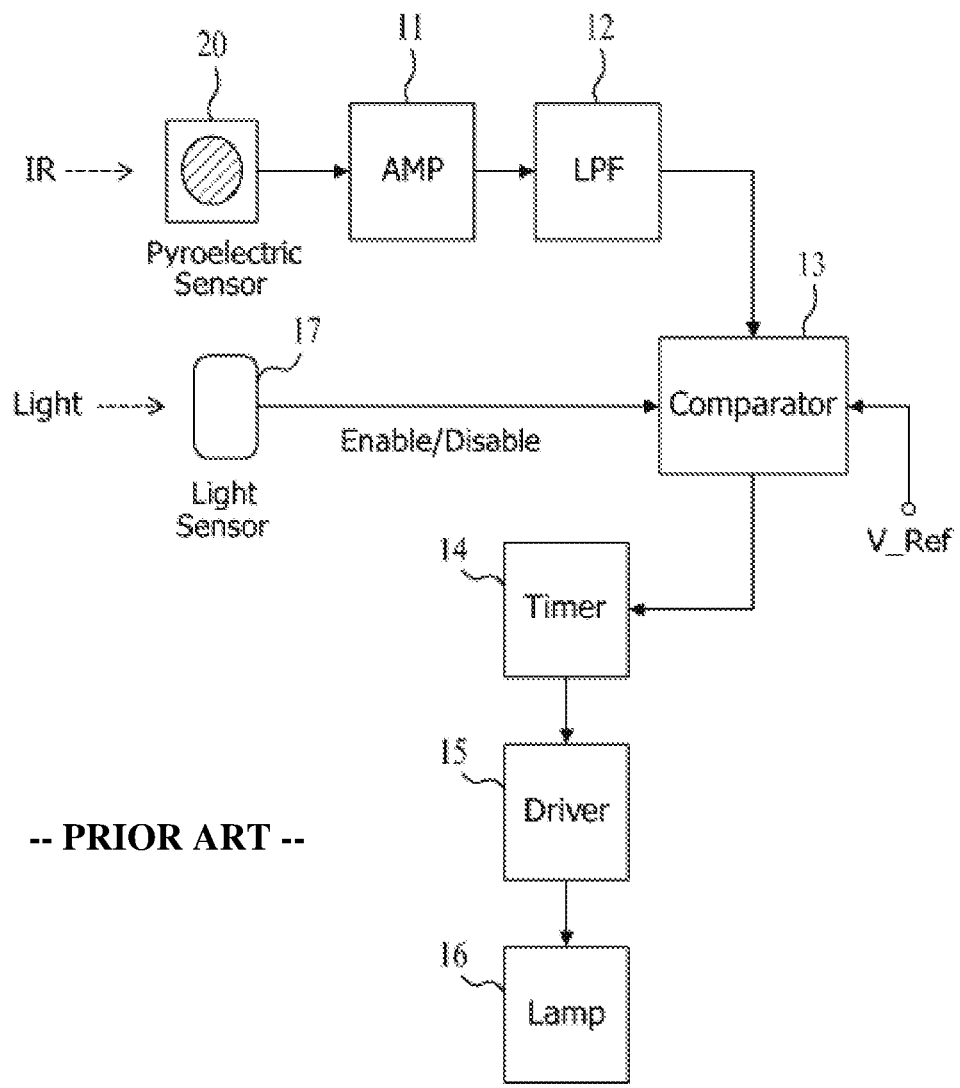
FIG. 2 illustrates a thermal detection device employing a thermopile sensor.
Figure 3:
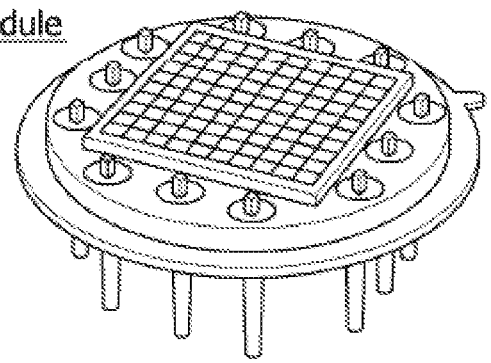
FIG. 3 illustrates a thermopile array sensor module.
Figure 4:
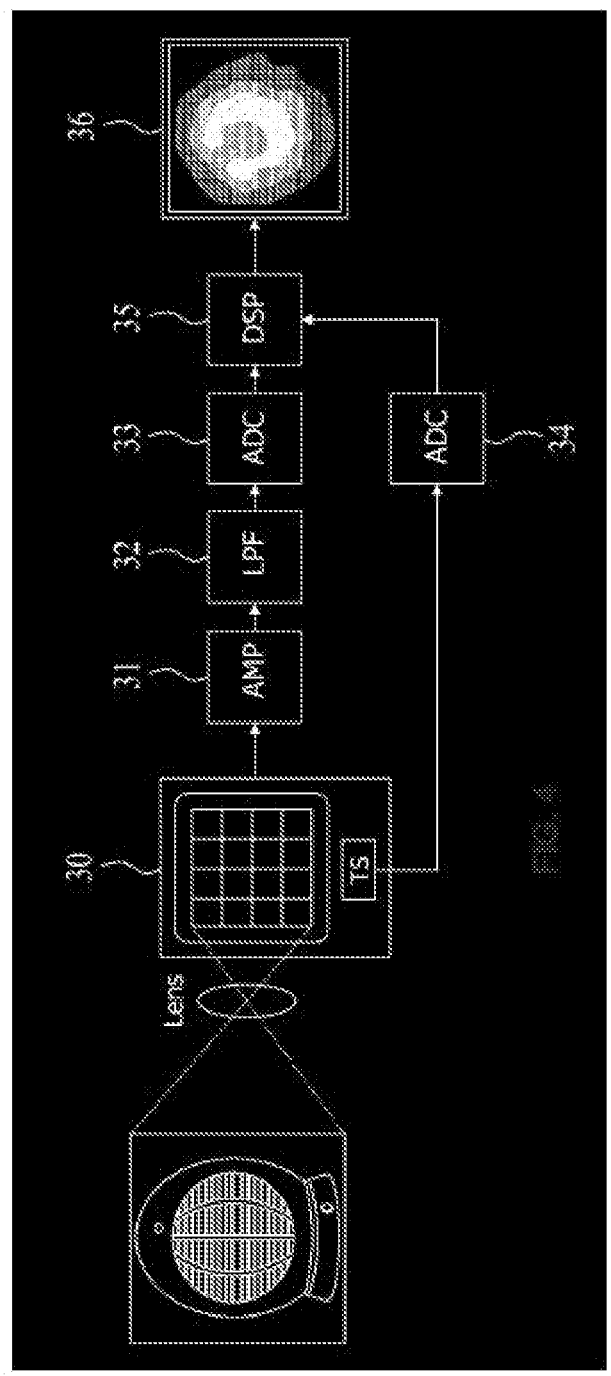
FIG. 4 illustrates a thermal picture measurement unit employing a thermopile array sensor module.
Figure 5:
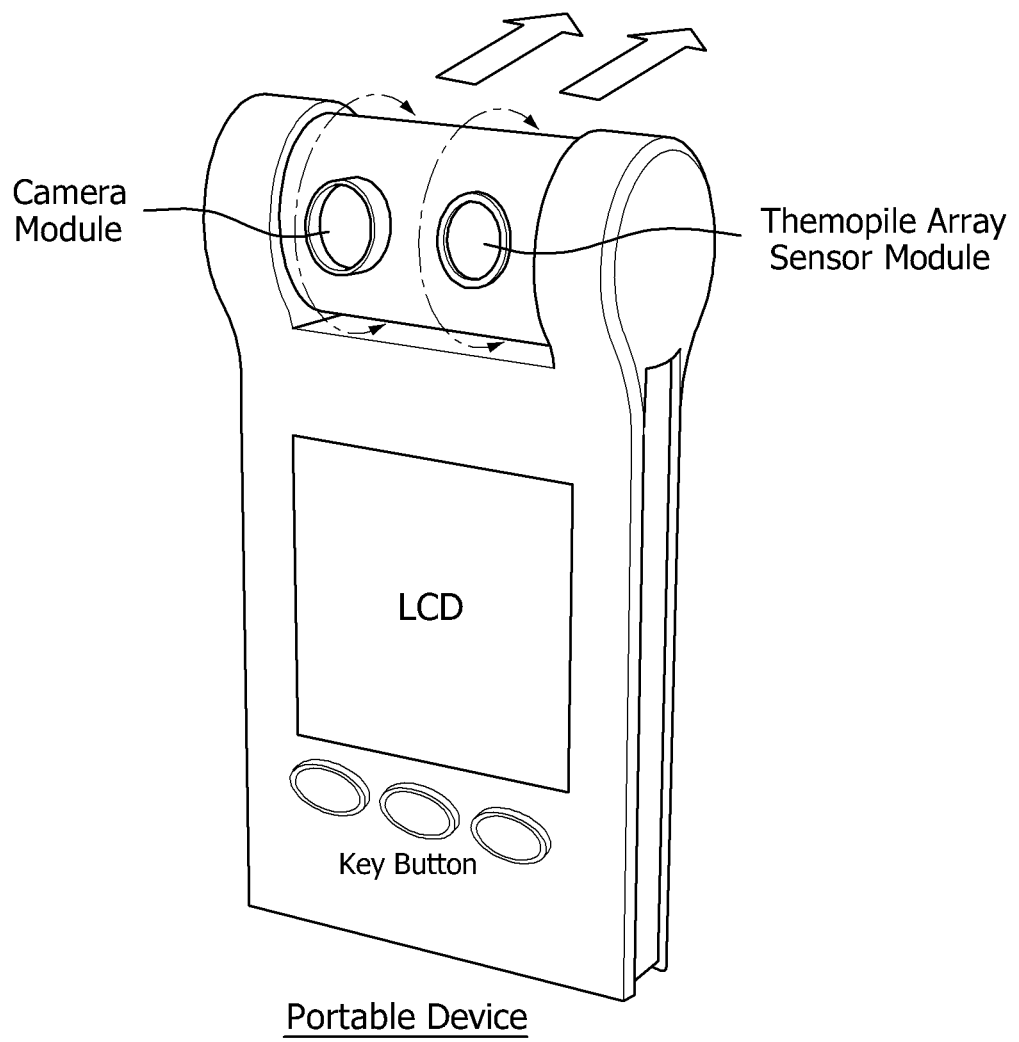
FIG. 5 illustrates an embodiment of the present invention applied to a portable device.

A device for measuring temperature with infrared array sensor may be configured by exemplarily including an infrared array sensor module, a camera module, and an electric circuit module controlling the other componential modules. In the configuration, the infrared array sensor module may be formed of a plurality of infrared sensors (e,g. thermopile sensors) as like a thermopile array sensor. The infrared sensors are arranged in an pixel array, each corresponding to each pixel, to acquire thermal picture information from a subject such as material or human body. The camera module is used for obtaining image information from a subject, including a camera device such as charge-coupled device (CCD) or complementary metal-oxide-semiconductor (CMOS) camera. In the mean time, as illustrated in FIG. 5, this device for temperature measurement may be applied to a portable device equipped with a camera module, a thermopile array sensor (TAS) module, a display module, key buttons, and so on. The camera module and the thermopile arrays sensor module, for instance, may be fixed side by side in the opposite or same direction with the display module. Otherwise, as shown in FIG. 5, the camera module and the thermopile array sensor module may be installed to be rotatable over 180° by means of a revolving member, facing the opposite or same direction with the display module. Otherwise, the device for temperature measurement may be fixedly set at a specific position of the portable device.

Figure 6:
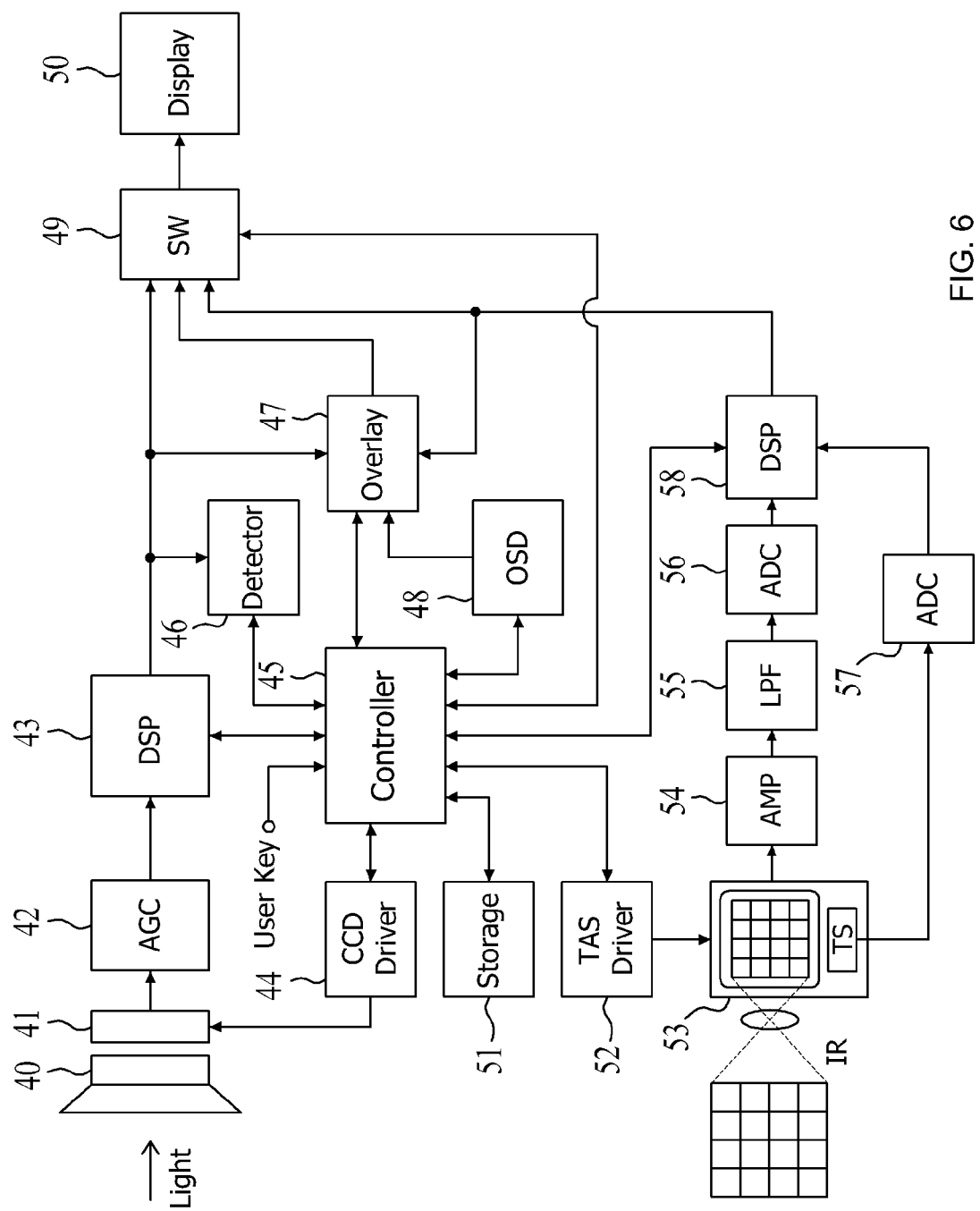
FIG. 6 illustrates a configuration of a portable temperature measurement device according to an embodiment of the present invention.

Now FIG. 6 will be referred to detail a configuration and operation of the temperature measurement device according to the present invention.

As aforementioned, the device can be organized including a camera module, an infrared array sensor module and an electric circuit module. In an embodiment, the camera module may be formed of lens member 40 and CCD 41. The infrared array sensor module may be formed of thermopile array sensor 53, amplifier (AMP) 54, low pass filter (LPF), first analogue-digital converter (ADC) 56, second analogue-digital converter (ADC) 57 and digital signal processor (DSP) 58. The electric circuit module may be formed including automatic gain controller (AGC) 42, digital signal processor (DSP) 43, CCD driver 44, controller 45, storage 51 and TAS driver 52.

The display module 50 may be used with a small LCD proper to the portable device, especially with an LCD including a touch screen in consideration for simplicity of key buttons and convenience in use.

On display module 50 can be selectively represented camera image information taken by CCD 41, thermal picture information measured by thermopile array sensor 53, or an overlap with the camera image and thermal picture information. Further, an indicator provided from on-screen display (OSD) module 48, which will be described later, may be overlapped with camera image and/or thermal picture on display module 50. For this operation, controller 45 functions to control OSD module 48 in response to a user key input, enabling various menu styles and OSD images (i.e. indicators in multiple forms) to be expressed on display module 50.

Figure 7:
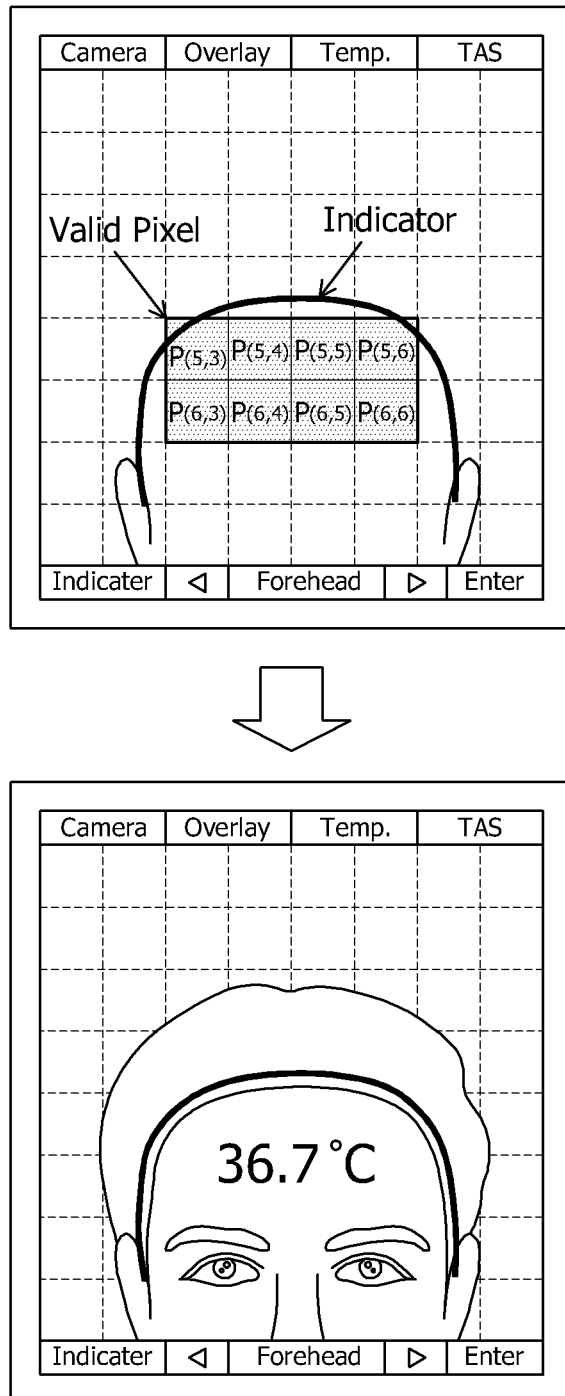
FIG. 7 illustrates an embodiment displaying an indicator for a human forehead.

As an example, if a user want to measure a thermal picture only from a person's forehead (as a subject), controller 45 forces OSD module 48, referring to FIG. 7, to express an indicator, which has an edge line corresponding to a shape of the forehead, in display module 50.

An indicator has a profile corresponding to the whole or local shape of a subject. Here, a region expressed by an indicator is defined as a target point (the whole or local region of a subject) to be measured for exact temperature by a user. Information about concrete shape and displayed point of an indicator is reserved and managed in storage 51 in advance on basis of a beforehand experimental result so as to provide an appropriate ranges of distance and angle for measurement to the forehead.

Controller 45 also forces switch (SW) 49, while an indicator is being shown, to enable camera image information of CCD 41 and/or thermal picture information of the thermopile array sensor to be overlapped on display module 50. Then, a user adjusts the forehead's part, which is displayed by a camera image, by a distance and angle to match with an edge line of the indicator.

When a user pushes a key button for measurement after matching the forehead part with the indicator through the aforementioned process, controller 45 may enable thermopile array sensor 53 by controlling TAS driver 52.

An electric signal output from thermopile array sensor 53 is processed as the thermal picture information by way of amplifier 54, low pass filter 55, first analogue-digital converter 56, and digital signal processor 58. This thermal picture information means temperature values acquired first by the plural thermopile sensors. Controller 45 calculates and converts the electric signal values, which are each detected by the thermopile sensors, with reference to the sensor correction data that have been stored in advance. Controller 45 can also make display 50 express the thermal picture information that varies in color depending upon a temperature value measured by pixel.

During this, for rendering each pixel value of the thermopile array sensor to have a reasonable temperature value, an additional sensor is used for measuring internal sensor temperature that is applied to compensating a temperature value obtained by each infrared sensor. In other words, first assuming that internal sensor temperature is identical to ambient temperature around a subject, the value taken by each pixel (i.e. each infrared sensor corresponding thereto) is corrected upon which an internal sensor temperature measured by the additional sensor of the infrared sensor is the ambient temperature.

Here, as using a thermistor sensor of nonlinear logarithmic function as a temperature sensor degrades accuracy of measurement for sensor itself, the present invention employs for example a proportional-to-absolute temperature (PTAT) sensor characterized in linear operation with the first order function to enhance accuracy of temperature measurement for sensor itself. With the PTAT sensor, a process for compensating a temperature value can be easier.

In an embodiment, all of four PTAT sensors are settled respectively at the corners of the thermopile array sensor. Then, by adopting an average temperature value of the PTAT sensor as sensor temperature, measured values are corrected. While finally choosing the average value of the four PTAT sensors, there is a condition before accepting the average value. That is, a stable condition is not recognized until temperature distribution ranges of the PTAT sensors are all measured within the scope of ±0.2° C., then the average value is taken and finally used as a value of the internal sensor temperature.

In the meantime, while thermal picture information (i.e. a subject's thermal picture) or image information (i.e. a subject's camera image) is being expressed on display module 50 together with an indicator, a user adjusts a position of the device or the subject to overlap a target point of the subject with the indicator. After that, temperature is measured to the target point of the subject. During this, for exact temperature measurement to the target point, the following way according to the present invention is carried out to detect temperature from the subject.

In an embodiment, with determination that pixels placed within an indicator overlapping a target point of a subject are 'valid pixels', the resultant temperature value is calculated based on temperature values detected by the thermopile sensors corresponding to these valid pixels. Exemplarily, for an 8×8 array sensor, 64 pixel values are obtained in total. Since all of pixel data cannot be reasonable, pixels to be effectively used for temperature measurement are determined as valid pixels. Referring to FIG. 7, among 8×8 pixels of thermopile array sensor 53, those corresponding to the forehead defined by the indicator, e.g. $P_{(5,3)}$, $P_{(5,4)}$, $P_{(5,5)}$, $P_{(5,6)}$, $P_{(6,3)}$, $P_{(6,4)}$, $P_{(6,5)}$ and $P_{(6,6)}$, are only selected as valid pixels and used for calculating bodily temperature of the person as a subject.

During this, if the measurement is carried out such that a thermometer is spaced beyond a reference distance from a subject's face, it is difficult to acquire exact temperature values because a pixels region covered by the sensor is extended due to a broadened field of view (FOV). Therefore, such valid pixels can be obtained by confining the subject's face within the reference distance. Especially, in the temperature measurement device according to the present invention, a distance and angle for measurement can be first adjusted appropriately to a subject by matching the subject's target point, which is represented in thermal picture information (or camera image information), with an edge line of an indicator.

In another embodiment for pixel validation, pixels whose data are within a predetermined temperature range (e.g. 30.0~40.0° C. for human body) are determined as valid pixels. Thus, other pixel data out of the temperature range are abandoned from the measurement because they are not relative to a human body.

Meantime, as it is difficult to obtain an exact temperature value if the subject is shaking too much, the following way is permissible to determine valid pixels so as to conduct measurement in a stabilized condition by finding a status of movement.

In an embodiment, at the beginning of measurement with 8×8 sensors, 64 temperature values are taken per frame from the thermopile array sensor. Each frame may be an aggregation of pixel data. A movement of the subject can be found by comparing signals provided in the unit of frame.

For instance, assuming that 2 frame signals are defined as x(i) and y(i) by a cross-correlation mode, a cross-correlation value r to a delay value d between the frames may be given by $$r(d) = \frac{\sum_i [(x(i) - mx) \times (y(i-d) - my)]}{\sqrt{\sum_i (x(i) - mx)^2} \sqrt{\sum_i (y(i) - my)^2}}.$$

From the equation, the parameters mx and my mean average values for 2 frames. A pixel value, which is an x-axis value of a part where a peak appears among these cross-correlation values, represents a shift distance as a delayed value of two frames.

Exemplarily, if an x-axis value of a part where a peak of the cross-correlation value appears is −2, this means there is a shift by 2 pixels. The sign "−" represents that an image at frame #2 is shifted upward. And, with a pixel size and a data acquisition time between frames, a shift rate of a subject can be obtained through a short operation.

In this embodiment, if a time for measurement is set to be 2 seconds, a subject should be restricted in the minimum motion for the 2 seconds. Further, by restricting a shift distance within 2 pixels by means of the aforementioned cross-correlation mode, a normal resultant value of temperature measurement can be instructed only when both x- and y-peak values of the cross-correlation are less than ±2.

The aforementioned pixel validation may be carried out independently or duplicated. In an embodiment, pixels included in an indicator are first determined as valid ones and next the resultant valid pixels having temperature values included in the human temperature range are chosen from the first selected pixels. Additionally, if the number of valid pixels does not correspond to a predetermined range, the temperature measurement can be repeated after the former measurement has been carried out beyond the reference distance.

According to embodiments of the present invention, while a distance and angle for measurement can be first adjusted by overlap between a subject's thermal picture (or a camera image) and an indicator, it is possible to further improve the accuracy of distance adjustment by additionally conducting the aforementioned pixel validation.

Controller 45 determines valid pixels in the manner described above and calculates the resultant temperature value detected from a subject with reference to the valid pixels' data (i.e. temperature values measured by the infrared sensors corresponding to the valid pixels).

In addition, according to this invention, ambient temperature can be measured more exactly with reference to other pixels but valid pixels, through which the resultant temperature value can be corrected more precisely.

First, assuming that 'Ts' represents a temperature conversion value according to a detection amount of infrared rays measured by the infrared sensors each forming the pixels and that 'Tpyro' represents an internal sensor temperature value measured by the temperature sensor, pixel data 'Tp' corresponding respectively to the infrared sensors is equal to a sum of Ts and Tpyro (i.e., Tp=Ts+Tpyro). Therefore, a thermal picture is first displayed based on each pixel data like the aforementioned.

Next, after correspondingly generating an indicator at a target point marked by a subject's thermal picture (taken by the infrared array sensor) or image (taken by the camera), the indicator is controlled to overlap the thermal picture or camera image. Then, controller 45 enables the infrared array sensor to measure temperature from the subject.

During this, controller 45 determines valid pixels in the aforementioned manner. And, an ambient temperature value 'Tamb' is calculated from pixel data of other pixels (invalid pixels) but the valid pixels. Tamb may be given by a function of invalid pixel data Tpn and Tpyro (Tamb=f(Tpn,Tpyro)). With this ambient temperature value, each valid pixel data Tpe can be compensated. Compensated valid pixel data Tpec may be given by a function of the valid pixel data Tpe before compensation and the ambient temperature value Tamb (Tpec=f(Tpe,Tamb)). Thus, the resultant temperature value can be output from the compensated valid pixel data.

Although internal sensor temperature is measured relatively and exactly by means of the PTAT sensor, it can be basically different from ambient temperature. Therefore, for exact temperature measurement to a subject's target point, it needs a circumstance where a value of Tpyro on which Tp is based is similar to ambient temperature around the subject. In the prior arts, as there has not been proposed any other proper way for accurately measuring ambient temperature around a subject, it is just recommended to conduct temperature detection after leaving a thermometer for a long time in a circumstance at which its temperature measurement device will be used. Different from that, according to the present invention, Tp is first valued from Tpyro on, in which a subject's ambient temperature value can be calculated with reference to data of invalid pixels, but valid pixels, against the circumstance thereof. For instance, if ambient temperature value Tamb is different from a value of Tpyro, controller 45 may inform a user, through display module 50 or another notifying means (e.g. speaker, etc), of an inadequate circumstance for temperature measurement. Further, controller 45 may compare ambient temperature value Tamb with Tpyro. If an error resulting from the comparison is within a predetermined range, controller 45 determines a current circumstance as suitable for temperature measurement, guiding a user thereto.

In an embodiment, ambient temperature values calculated from invalid pixels can be used for correcting valid pixel data and the corrected valid pixel data can be used for calculating the resultant temperature of a subject. For instance, in case of detecting bodily temperature, data taken by the thermopile sensors corresponding each to valid pixels is a temperature value on a subject's face. This face temperature is lower than an actual bodily temperature, so it is necessary to conduct a process for converting the face temperature value into the actual bodily temperature value, as follows.

For the purpose of obtaining a relation between actual bodily temperature and pixel temperature taken by the infrared sensors, a clinical experiment was conducted with 200 persons (normal 100 and feverish 100). The experiment was progressing by first collecting pixel temperature values through the array sensors of the device according to the present invention and taking temperature of oral cavities through contacting electronic thermometers used in hospitals, during which temperature measurement was carried out 5 times in all.

From clinical data collected by the experiment, while data of the array sensor are fully 64 if the pixels are formed in 8×8, valid pixels are chosen as stated above and then the maximum values indicating the highest temperature values among the array sensor data (or pixel data) are used as face temperature values on the subjects. After obtaining averages of the maximum values from the 5-times array sensor data collected by the subjects, these averages are applied to a comparison table along with averages of the 5-times oral cavity temperature values. A resultant conversion table is obtained by setting an X axis for face temperature values (the maximum values of the pixel data) while setting Y axis for the oral cavity temperature values. The conversion table is composed in a form of look-up table (LUT) programmed into a ROM of a microprocessor, in which actual temperature value is calculated by putting the measured values into the X axis and then converting the Y-axis values through linear interpolation.

In an embodiment, controller 45 may help exact measurement to face temperature values by granting a weight for data before converting valid pixel data into bodily temperature values if ambient temperature values taken by invalid pixels is lower than 16°. Additionally, controller 45 may even exclude pixel data of the highest and lowest temperature, for data accuracy, in outputting an average temperature value of valid pixels.

According to embodiments of the present invention, it is achievable for accurate temperature measurement by pixel validation, ambient temperature compensation, bodily temperature conversion with look-up table. Especially, since the plurality of infrared sensors each capable of detecting temperature to local points are correspondingly arranged in pixels of array, it is possible to exactly measure a subject's bodily temperature with reference to pixel data obtained from once taking thermal picture without moving the device.

In an embodiment, controller 45 enables OSD module 48 to express letters for the calculated average temperature (e.g. 36.7°) on display module 50. Thus, a user is able to select the forehead in convenience and obtain a thermal picture therefrom, as well as measuring temperature corresponding to the forehead.

Moreover, controller 45 is operable to control detector 46 to take a forehead profile by scanning a digitized camera image and then begin thermal picture measurement at the time when the camera image matches with the indicator.

On display module 50 can be expressed, as illustrated in FIG. 7, a menu item for camera images (e.g. 'Camera'), a menu item for an overlap with a camera image and a thermal picture (e.g. 'Overlay'), a menu item for a result of temperature measurement (e.g. 'Temp'), and a menu item for a thermal picture taken by the thermopile array sensor (e.g. 'TAS').

From display module 50, a user is also able to identify and handle other items, i.e., a current indicator (e.g. 'Forehead'), a selection item for another indicator such as ear, hand, etc. (e.g. left and right arrows), and a selection item for beginning the thermal measurement (e.g. 'Enter').

In an embodiment, controller 45 enables OSD module 48 to display an indictor that is requested as another one by a user who pushes down the selection item or another key button.

Figure 8:
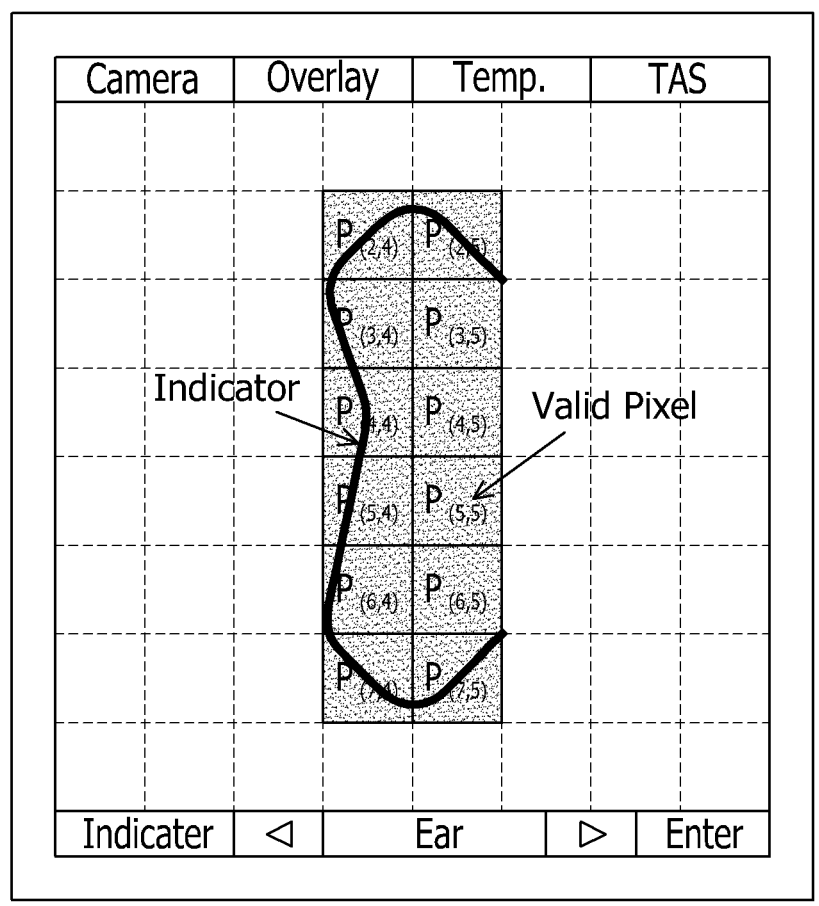
FIG. 8 illustrates an embodiment displaying an indicator for a human ear.

For example, referring to FIG. 8, if a user wants to measure temperature from a human ear, controller 45 enables OSD module 48 to express an ear-shaped indicator on display module 50. During this, pixels (e.g. $P_{(2,4)}$, $P_{(2,5)}$, $P_{(3,4)}$, $P_{(3,5)}$, $P_{(4,4)}$, $P_{(4,5)}$, $P_{(5,4)}$, $P_{(5,5)}$, $P_{(6,4)}$, $P_{(6,5)}$, $P_{(7,4)}$ and $P_{(7,5)}$) corresponding to the ear among the thermopile array sensors of 8×8 are selected as valid pixels to calculate their temperature value.

Figure 9:
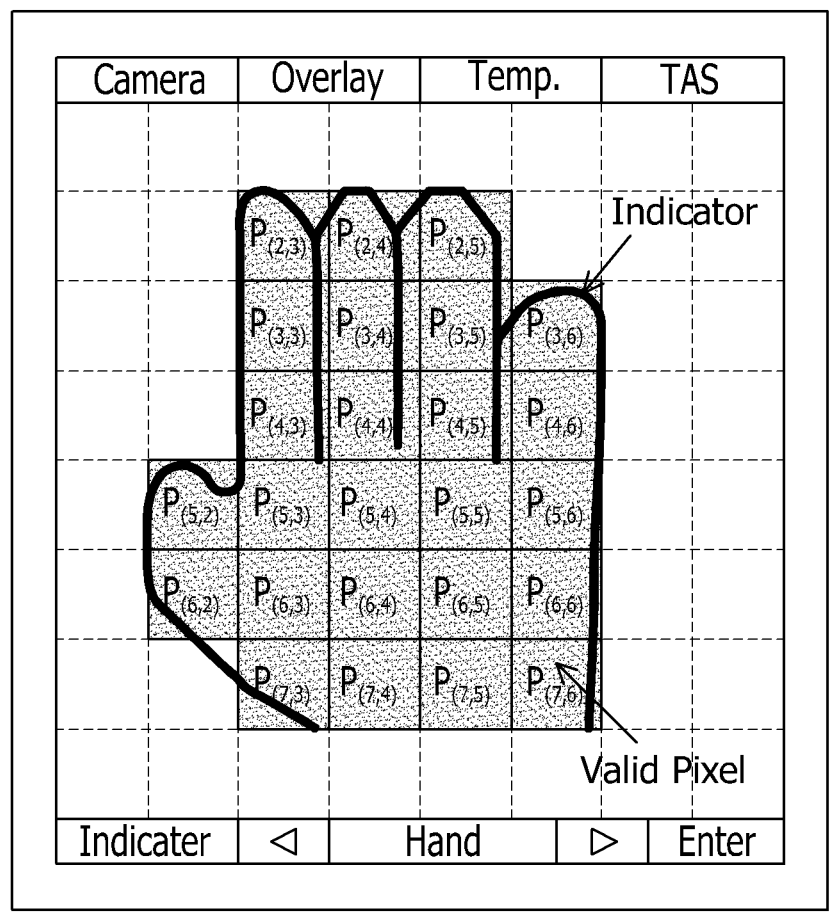
FIG. 9 illustrates an embodiment displaying an indicator for a human hand.

As also, referring to FIG. 9, if a user wants to measure temperature from a human hand, controller 45 enables OSD module 48 to express a hand-shaped indicator on display module 50. During this, pixels (e.g. $P_{(2,3)}$, $P_{(2,4)}$, $P_{(2,5)}$, $P_{(3,3)}$, $P_{(3,4)}$, $P_{(3,5)}$, $P_{(4,3)}$, $P_{(4,4)}$, $P_{(4,5)}$, $P_{(5,2)}$, $P_{(5,3)}$, $P_{(5,4)}$, $P_{(5,5)}$, $P_{(6,2)}$, $P_{(6,3)}$, $P_{(6,4)}$, $P_{(6,5)}$, $P_{(6,6)}$, $P_{(7,3)}$, $P_{(7,4)}$, $P_{(7,5)}$ and $P_{(7,6)}$) corresponding to the ear among the thermopile array sensors of 8×8 are selected as valid pixels to calculate their temperature values.

Figure 10:
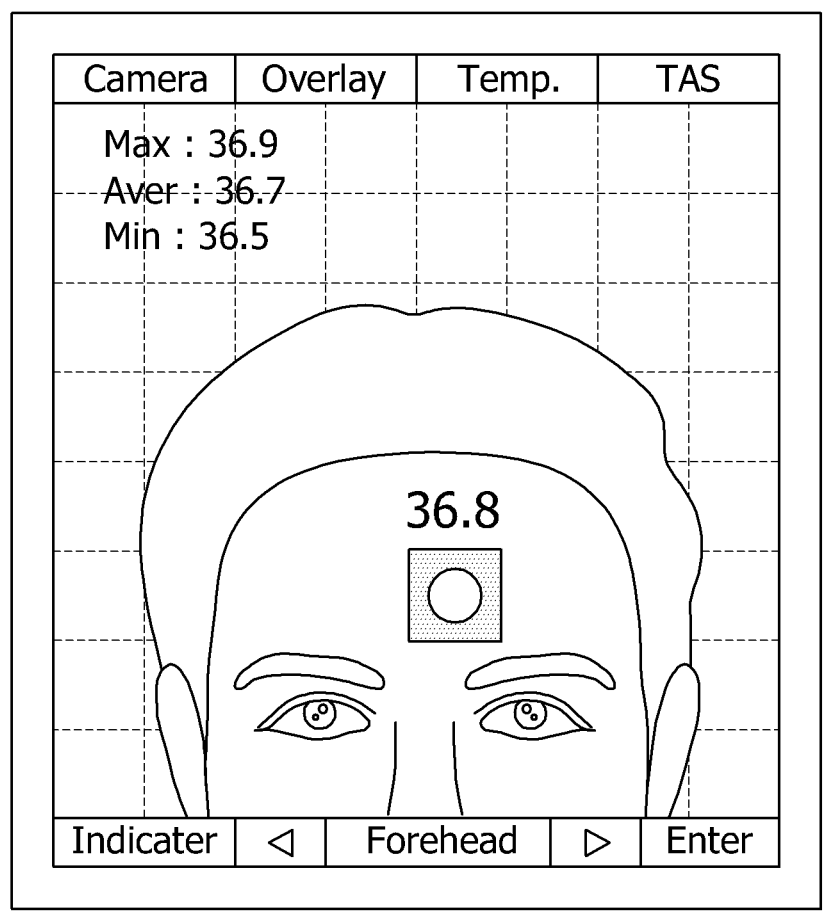
FIG. 10 illustrates another embodiment displaying temperature of a specific part by a user's touch.

Now referring to FIG. 10, if a user requests, controller 45 may calculate the resultant temperature value from an average temperature value (e.g. 36.7°) of the valid pixels and then express the average temperature value on display module 50. Controller 45 may also enable to coincidently display the highest and lowest temperature values (e.g. 36.9° and 36.5°) of the valid pixels.

Furthermore, in the course of calculating the resultant temperature value from the average temperature value, controller 45 may exclude the highest and lowest temperature values to stabilize the average, or grant a higher weight (e.g. 120%) to temperature values of pixels disposed at the center of the valid pixels while a lower weight (e.g. 80%) to temperature values of peripheral pixels.

In case of employing an LCD with touch screen function for display 50, as illustrated in FIG. 10, when a user touches a specific position on the LCD, controller 45 also enables OSD module 48 to mark a temperature value (e.g. 36.8°) of a pixel (e.g. $T_{(6,5)}$) corresponding to the specific position after finding a coordinate of the position.

Figure 11:
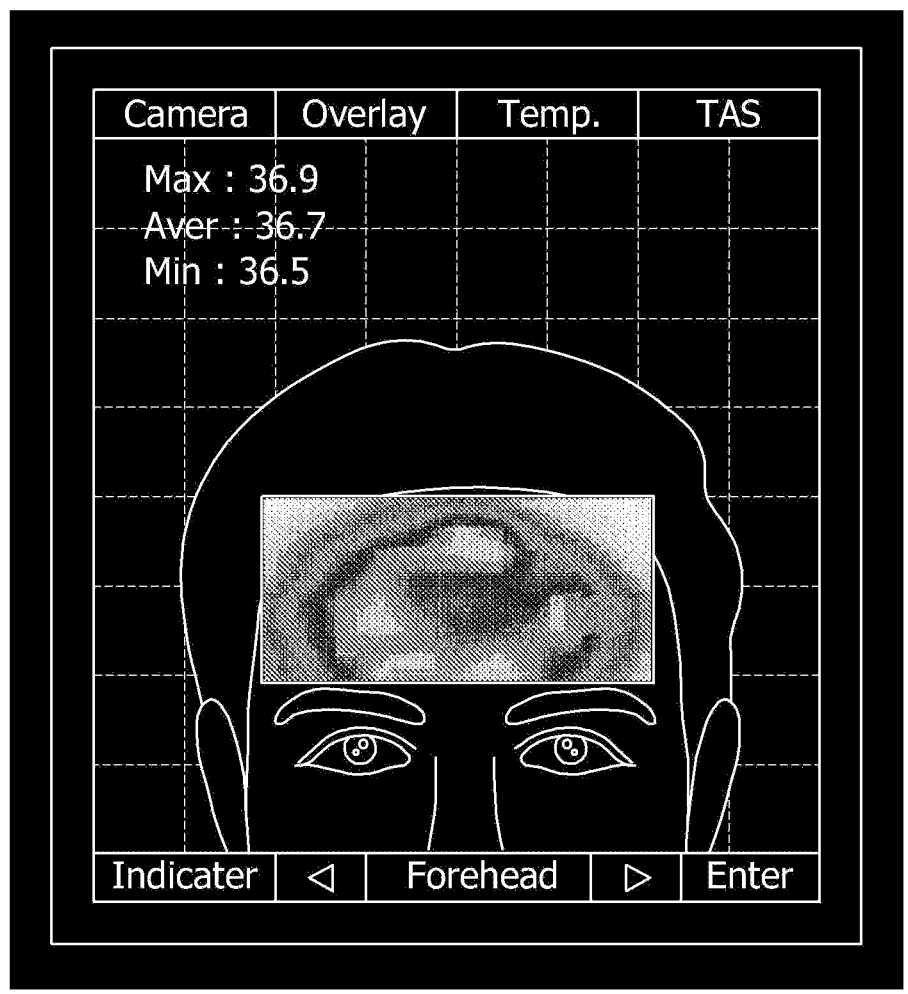
FIG. 11 illustrates an embodiment displaying by overlay between a thermal picture and a camera image for a human forehead.

Additionally, referring to FIG. 11, if a user selects the menu item of 'Overlay', controller 45 enables overlaying part 47 and switch 49 to overlapping a camera image and a thermal picture on display module 50. Therefore, a user is able to easily identify thermal distribution at the forehead.

Meanwhile, if a temperature value measured by the aforementioned process is determined as abnormal out of the predetermined reference temperature range, controller 45 enables storage 51 to reserve information about camera image, thermal picture and temperature in order to make a user replay and watch them.

In an embodiment, the temperature measurement device according to the present invention may be additionally provided with a wired or wireless communication module. In this case, controller 45 may transfer information of camera image, thermal picture and temperature from storage 51 to a computer or server coupled thereto by way of a wired or wireless communication network.

Figure 12:
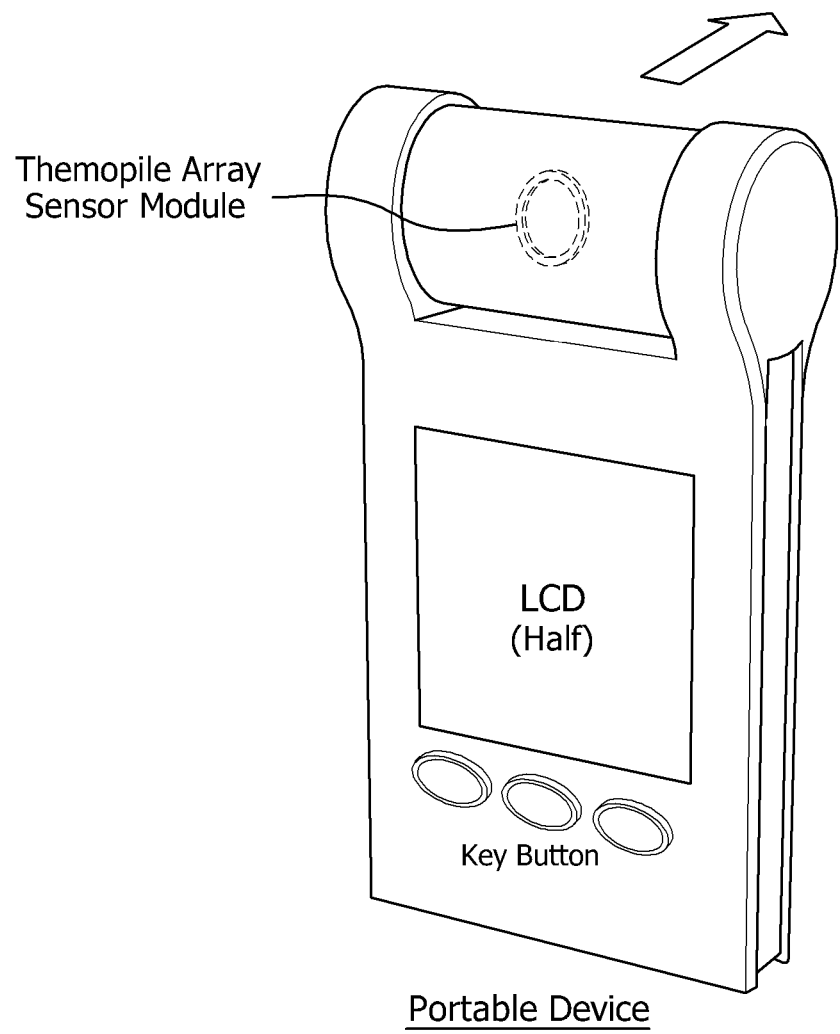
FIG. 12 illustrates another embodiment for a portable temperature measurement device according to the present invention.

As another embodiment according to the present invention, referring to FIG. 12, a device for temperature measurement may be comprised of a translucent LCD as the display module.

Figure 13:
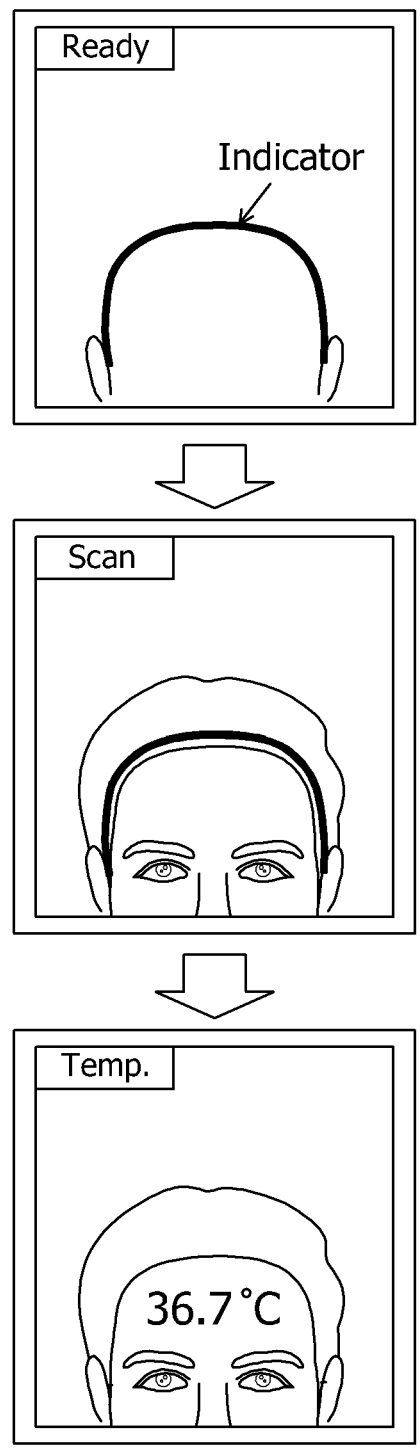
FIG. 13 illustrates an embodiment displaying an indicator on a translucent LCD screen for a human forehead.

In this case, a user is able to directly identify a subject's shape, instead of a camera image, exposed through a transparent or translucent LCD in the naked eye. During this, on the transparent or translucent LCD can be reflected a variety of indicators proposed as above. For instance, referring to FIG. 13, when an indicator illustrating a human forehead is represented on the transparent or translucent LCD, a user is able to suitably adjust a distance and angle for measurement by handling coherence between a target point and the indicator while directly watching a subject's shape, which is being transmitted through the LCD, to the naked eye.

And, if the user pushes down a key for taking a thermal picture, as described in conjunction with FIG. 7, a process for measuring the thermal picture and temperature is carried out by way of pixel validation, ambient temperature compensation and so on.

Figure 14:
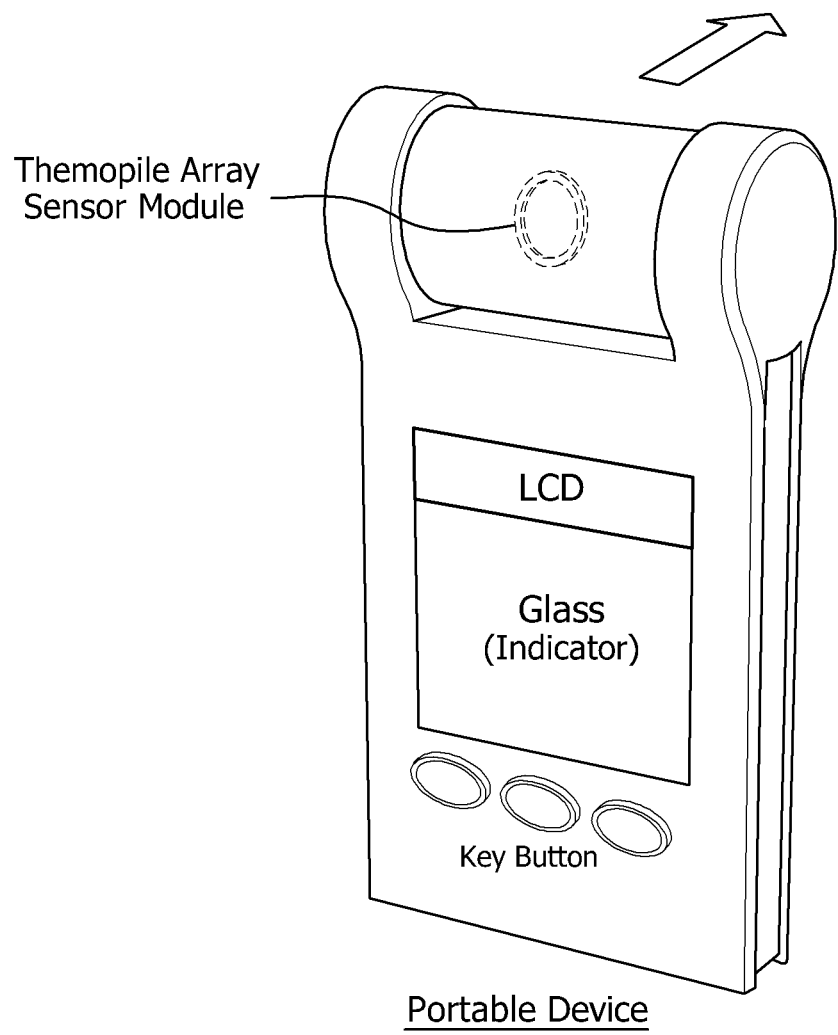
FIG. 14 illustrates another embodiment of a portable temperature measurement device according to the present invention.
Figure 15:
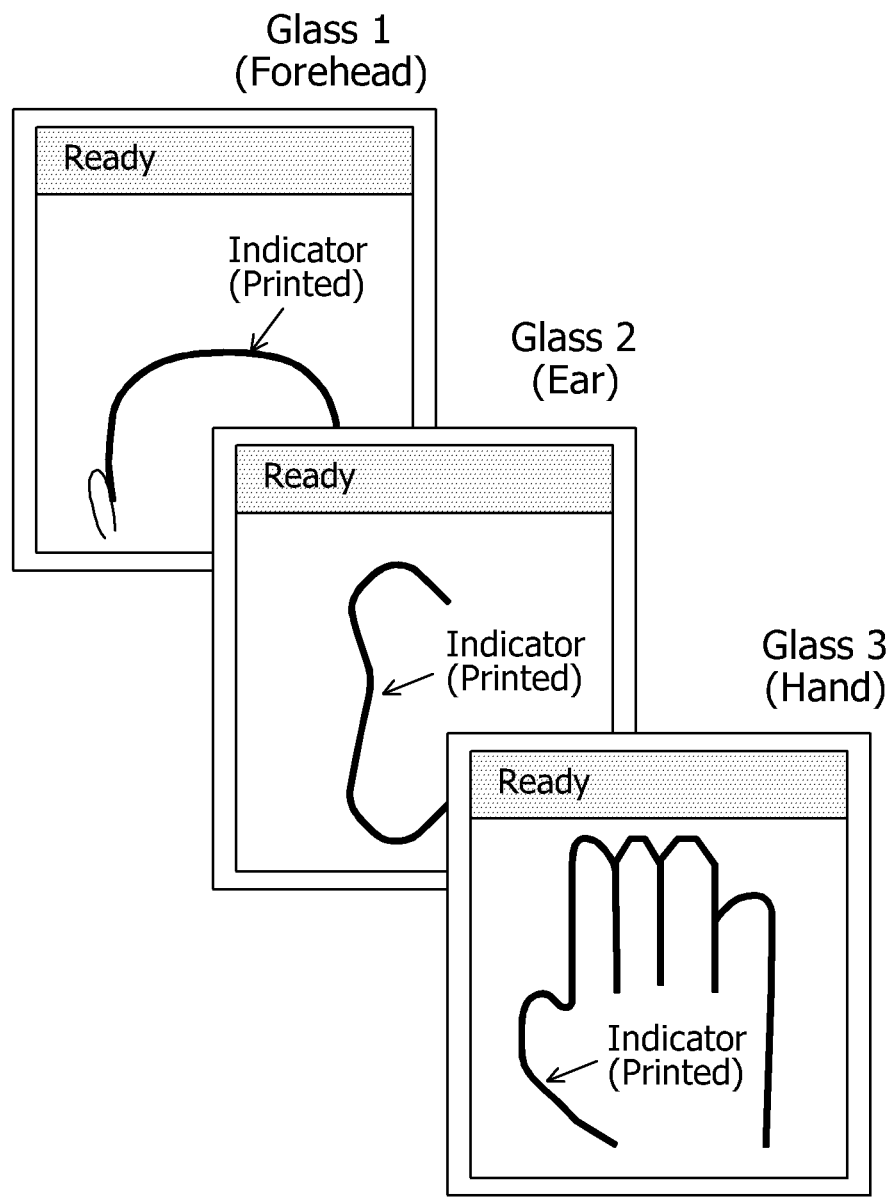
FIG. 15 illustrates an embodiment printing various indicators on different transparent glass windows.

In another embodiment, referring to FIG. 14, a temperature measurement device according to the present invention may be comprised of a transparent glass window along with an LCD as the display module, In this embodiment, a cheaper small or translucent LCD may be provided at the top of the transparent glass window, displaying the least message. On the transparent glass window can be printed an indicator with a shape in a form of a label. For instance, referring to FIG. 15, a user is able to change a label in which another indicator is printed.

Figure 16:
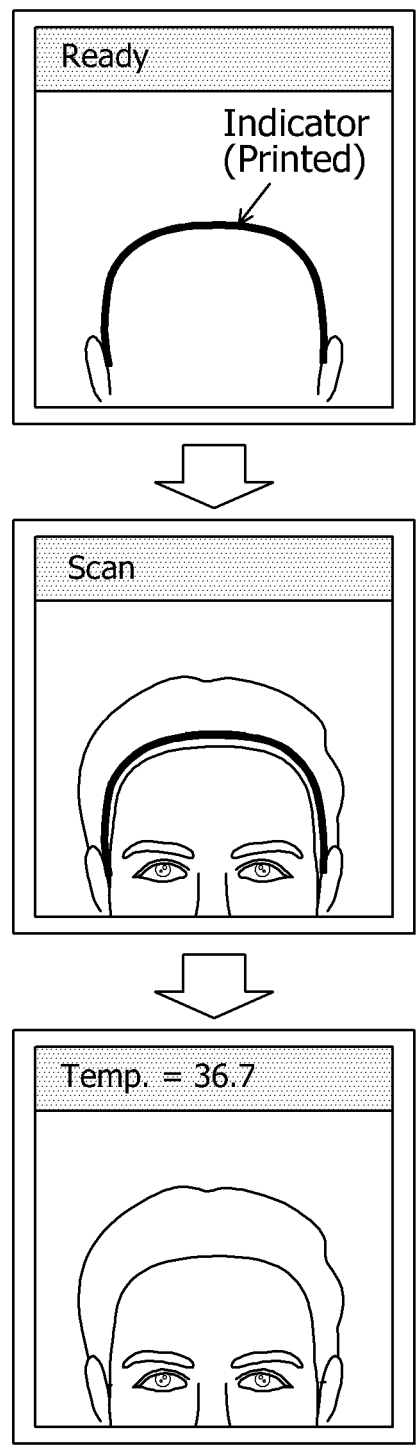
FIG. 16 illustrates an embodiment printing an indicator on a transparent glass window for a human forehead.

Then, the user is able to properly adjust a distance and angle for measurement so as to match a target point of a subject with the indicator printed on the transparent glass window, looking at the subject's shape, instead of a camera image, transmitted through the transparent glass window in the naked eye. For example, as illustrated in FIG. 16, when an indicator corresponding to a human forehead is printed on the transparent glass window, a user is able to adjust a distance and angle suitable for the forehead while looking at the subject's shape through the transparent glass window in the naked eye.

In detail about this, it is permissible to employ a view finder that is made in a form of a transparent plate (glass or polymer resin) through which a subject's shape can be projected. Especially, in such a view finder may be formed an indicator of a specific pattern. And a concave or convex lens may be available in the indicator. This lens enables a target point of a subject to be expressed in the view finder with an appropriate distance (e.g. 40-50 cm) spacing between the present temperature measurement device and the subject.

Figure 17:
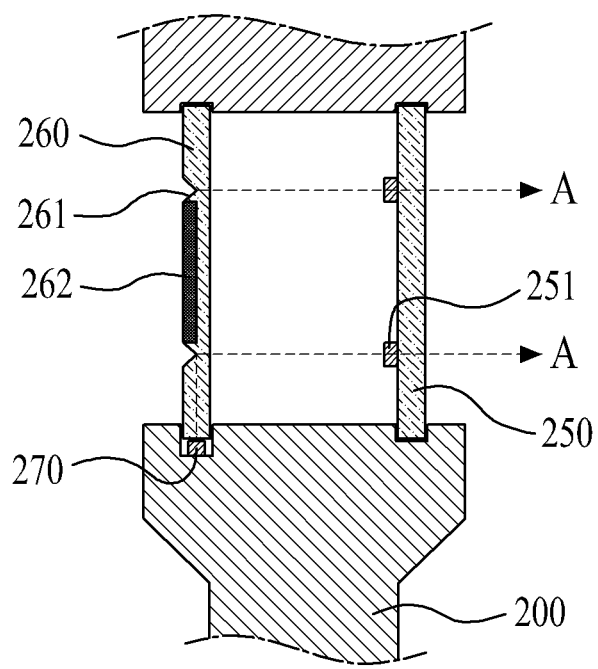
FIG. 17 illustrates another embodiment of a temperature measurement device, employing a view finder in which an indicator is displayed.
Figure 18:
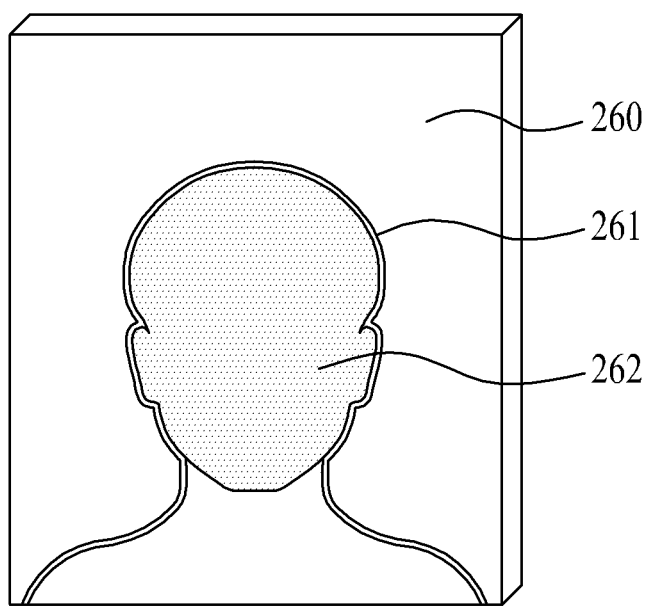
FIG. 18 is a perspective diagram of the view finder shown in FIG. 17.

With respect to a configuration of the view finder, referring to FIGS. 17 and 18, view finder 260 may be settled in case 200 of the device according to the present invention. An indicator can be displayed by way of notch 261 marked on a transparent plate forming view finder 260. This notch 261 may have a predetermined pattern (e.g. corresponding to a human forehead or the whole face), being engraved by a V-cut process. Additionally, in the indicator is formed lens 262 functioning as a concave or convex. Lens 262 may be formed of a Fresnel lens. A Fresnel lens is a kind of condensing lens made to have a small aberration with ring-shaped belts having prism effects for the purpose of reducing a lens thickness. It is possible for view finder 260 to be thinner by forming lens 262 in a Fresnel type. While the transparent plate can be entirely made of a Fresnel lens, it is preferred for lens 262 to be formed only at a region corresponding to a target point confined by an indicator (i.e. inner side of the indicator).

In case of using an LCD as the display module, as shown in FIG. 17, view finder 260 may be displaced with a predetermined interval from transparent LCD panel 250 in overlap. With this configuration, a user is able to identify a subject's shape through LCD panel 250 and view finder 260, and easily adjust a distance and angle so as to overlap a target point of the subject with the inside of the indicator. Specially, marker 251, which is formed on the surface of LCD panel 250 and has the same pattern with the indicator, may contribute to more exactly adjusting an angle of measurement to a subject by matching the indicator with the marker (i.e., it is possible to make parallelization to a direction of measurement). By adjusting an angle of infrared array sensor, and dispositions of the view finder and LCD, it becomes easier to make an infrared ray vertically incident on the infrared array sensor. In an embodiment, a light emission diode (LED) may be added to a lower side of view finder 260. In this configuration, notch 261 may be formed to make light, which is emitted from LED 270, vertically reflected on view finder 260 (i.e. vertical to the plate of the view finder, e.g. direction A in FIG. 18).

Figure 19:
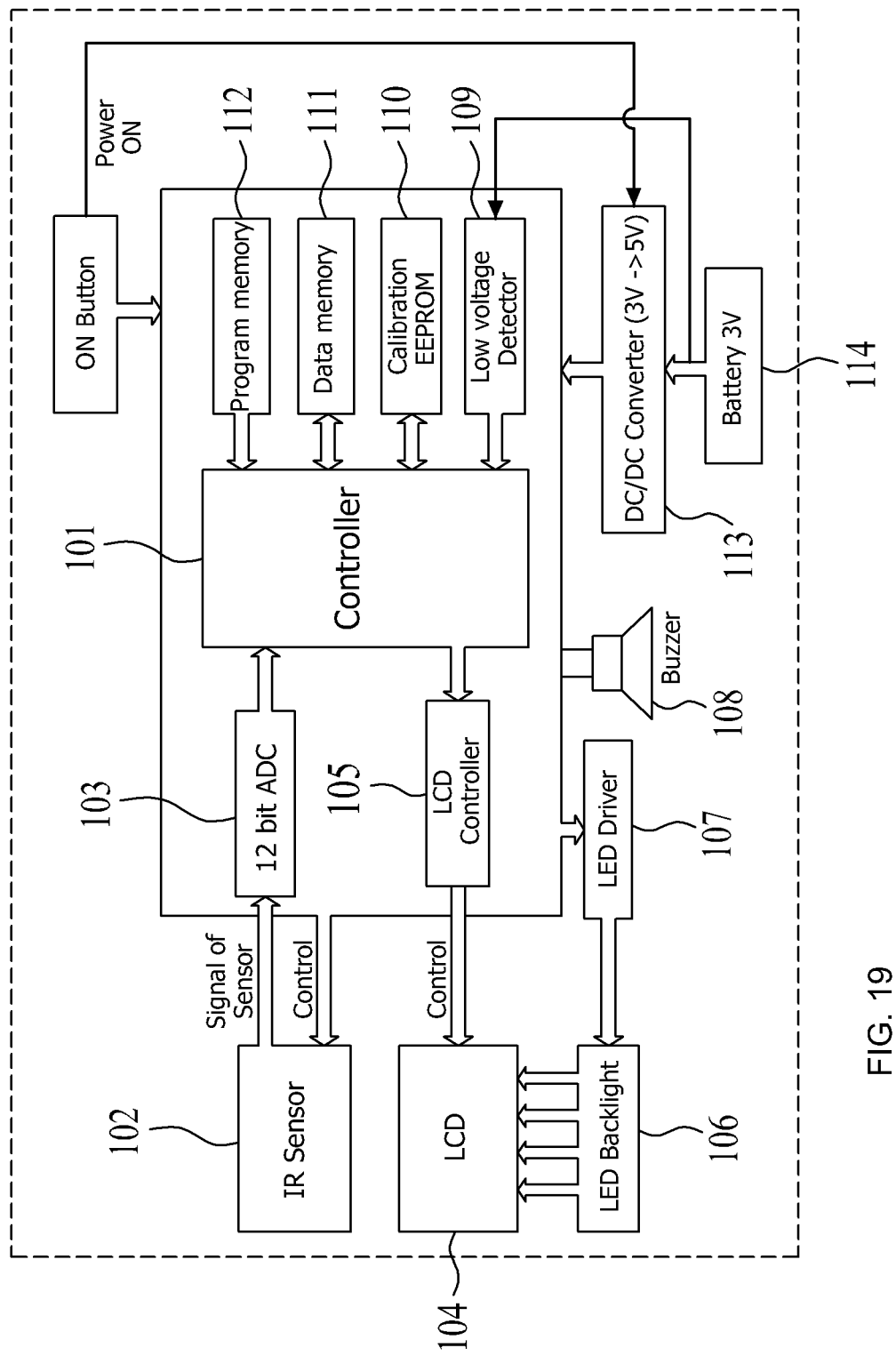
FIG. 19 is a circuit diagram illustrating another embodiment of a temperature measurement device according to the present invention.

FIG. 19 exemplarily shows a circuit organization of a portable temperature measurement device according to the present invention, employing such a transparent view finder instead of a camera module. As illustrated in FIG. 19, the device may be comprised of array sensor module 102 in which infrared sensors such as thermopile sensors are arranged in an 8×8 pixel array, analogue-digital converter (ADC) 103, an LCD 104, LCD controller 105, LED backlight 106, and LED driver 107. In addition, the device may include program memory 112, data memory 111, calibration EEPROM 110, low voltage detector 109, buzzer 108, DC-DC converter 113, and battery 114.

With this configuration of the portable temperature measurement device, if power is turned on by a user, a voltage applied to the battery is transformed into a predetermined voltage by way of the DC-DC converter. During this, low voltage detector 109 finds out whether the voltage applied to battery 114 reaches the predetermined voltage. If the voltage applied to battery 114 is lower than the predetermined voltage, controller 101 guides 'a low voltage' through buzzer 108, LVD 104 for the user. If there is a supply of an appropriate voltage, the controller 101 reads sensor calibration data from calibration EEPROM 110 and makes the sensor calibration data reside in program memory 112. The sensor calibration data is used for converting dimensions of electric signals, which are out each from the infrared sensors in response to intensity of infrared rays incident thereon, into temperature values. During this, when the user pushes down 'temperature measure key' after adjusting a distance and angle for measurement by means of the view finder, the electric signals measured respectively by the infrared sensors are converted into the temperature values. After reading temperature values corresponding each to the pixels of the infrared sensors, controller 101 operated to conduct the aforementioned algorithms of valid pixel reading, ambient temperature calibration, so that and the resultant temperature is exactly calculated to a target point of a subject and then expressed on the display.

Reading valid pixels may be carried out to determine pixels, which correspond to the plural infrared sensors whose temperature values are within a predetermined range, as valid. If the number of valid pixels is less than a predetermined count, controller 101 may enable sound or message about 'retry' to be noticed through buzzer 113, LED 106 or display 104, introducing the user into resuming temperature measurement.

It may be also possible to calculate an ambient temperature value with reference to temperature values measured by the infrared sensors corresponding to other pixels but the valid pixels. This ambient temperature value may be referred to re-correct pixel temperature values corresponding to the valid pixels, and calculate a resultant temperature by way of a predetermined temperature compensation table.

According to the embodiments about the device according to the present invention, since a thermal picture can be measured in convenience and accuracy by selecting a specific part of a person, e.g. forehead, ear, hand, etc., it enhances easiness on use and further improves reliability of measuring temperature and thermal distribution.

The foregoing is illustrative of exemplary embodiments and is not to be construed as limiting thereof. Although a few exemplary embodiments have been described, those skilled in the art will readily appreciate that many modifications are possible in exemplary embodiments without materially departing from the novel teachings and advantages. Accordingly, all such modifications are intended to be included within the scope of this invention as defined in the claims.

What is claimed is:

1. A portable device for measuring temperature, comprising:
   an infrared array sensor module configured to take temperature values in a unit of pixel, the module including a plurality of infrared sensors, wherein each infrared sensor of the plurality has an array of pixels;
   a controller configured to calculate a resultant temperature value of a subject with reference to the temperature values taken by at least one of the sensors in the infrared array sensor module;
   a display configured to express the resultant temperature value calculated by the controller; and
   a view finder configured to have an indicator defining a target point to be measured for temperature and having a profile corresponding to at least a portion of a shape of an anatomical part of the subject,
      wherein the view finder is formed of a transparent plate on which the subject's shape is reflected;
      wherein the transparent plate comprises a notch marked on the transparent plate and representing the indicator;
      wherein a lens is at least provided in a region confined by the indicator; and
      wherein, when the target point of the subject overlaps the indicator, the controller calculates the resultant temperature value of the subject.

2. The portable device according to claim 1, wherein the display is a transparent LCD panel and the view finder is configured to overlap with the LCD panel in a predetermined interval.

3. The portable device according to claim 2, wherein the LCD panel is configured to include a marker with a pattern; and wherein the pattern and the indicator of the view finder are the same in shape.

4. The portable device according to claim 1, further comprising an LED under the view finder, wherein the notch is configured to make light reflect vertically on the plate from the LED.

5. The portable device according to claim 1, wherein the controller is configured to, if temperature values measured each by the infrared sensors are within a predetermined range, determine that pixels corresponding to the infrared sensors are valid pixels, and calculate a resultant temperature value of the subject with reference to the temperature values measured by the infrared sensors corresponding to the valid pixels.

6. The portable device according to claim 5, wherein the controller is configured to calculate an ambient temperature value from the temperature values measured by infrared sensors corresponding to other pixels except the valid pixels, and correct the resultant temperature value of the subject with reference to the ambient temperature value.

7. A portable device for measuring temperature, comprising:
   an infrared array sensor module configured to take temperature values in a unit of pixel, the module including a plurality of infrared sensors, wherein each infrared sensor of the plurality has an array of pixels;
   a controller configured to calculate a resultant temperature value of a subject with reference to the temperature values taken by at least one of the sensors in the infrared array sensor module;
   a display configured to express the resultant temperature value calculated by the controller; and a view finder configured to have an indicator defining a target point to be measured for temperature, wherein the view finder is formed of a transparent plate through which the subject's shape is transmitted;

wherein the transparent plate comprises a notch marked on the transparent plate and representing the indicator;

wherein the notch has a predetermined pattern corresponding to at least a portion of a shape of an anatomical part of the subject; and wherein a lens is at least provided in a region confined by the indicator.

8. The portable device according to claim 7, wherein the display is a transparent LCD panel and the view finder is configured to overlap with the LCD panel in a predetermined interval.

9. The portable device according to claim 8, wherein the LCD panel is configured to include a marker with a pattern; and wherein the pattern and the indicator of the view finder are the same in shape.

10. The portable device according to claim 1, further comprising an LED under the view finder, wherein the notch is configured to make light reflect vertically on the plate from the LED.

11. The portable device according to claim 7, wherein the controller is configured to, if temperature values measured each by the infrared sensors are within a predetermined range, determine that pixels corresponding to the infrared sensors are valid pixels, and calculate a resultant temperature value of the subject with reference to the temperature values measured by the infrared sensors corresponding to the valid pixels.

12. The portable device according to claim 11, wherein the controller is configured to calculate an ambient temperature value from the temperature values measured by infrared sensors corresponding to other pixels except the valid pixels, and correct the resultant temperature value of the subject with reference to the ambient temperature value.

13. The portable device according to claim 7, wherein the resultant temperature is calculated from a cross-correlation of data from pixels.

* * * * *